United States Patent
Boehringer et al.

(10) Patent No.: US 7,815,616 B2
(45) Date of Patent: Oct. 19, 2010

(54) DEVICE FOR TREATING A WOUND

(75) Inventors: John R. Boehringer, Wynnewood, PA (US); John Karpowicz, Chester Springs, PA (US); Christopher L. Radl, Malvern, PA (US)

(73) Assignee: Boehringer Technologies, L.P., Phoenixville, PA (US)

( * ) Notice: Subject to any disclaimer, the term of this patent is extended or adjusted under 35 U.S.C. 154(b) by 1304 days.

(21) Appl. No.: 10/663,226

(22) Filed: Sep. 16, 2003

(65) Prior Publication Data

US 2004/0064132 A1 Apr. 1, 2004

Related U.S. Application Data

(60) Provisional application No. 60/410,718, filed on Sep. 16, 2002.

(51) Int. Cl.
A61M 1/00 (2006.01)
(52) U.S. Cl. .................. 604/313; 604/304; 604/305; 602/41
(58) Field of Classification Search ............. 604/304, 604/305, 307, 540, 541, 543, 313
See application file for complete search history.

(56) References Cited

U.S. PATENT DOCUMENTS

| 679,918 | A | 8/1901 | Shears |
| 697,637 | A | 4/1902 | Lee |
| 720,812 | A | 2/1903 | Johnson |
| 843,674 | A | 2/1907 | Funk |
| 1,066,934 | A | 7/1913 | Manney |
| 1,251,258 | A | 12/1917 | Magill |
| 1,355,679 | A | 10/1920 | McConnel |
| 1,385,346 | A | 7/1921 | Taylor |

| 2,025,492 | A | 11/1934 | Aird |

(Continued)

FOREIGN PATENT DOCUMENTS

EP 0 619 105 A1 10/1994

(Continued)

OTHER PUBLICATIONS

Morykwas, M. et al, "Vacuum-assisted Closure: A New Method for Wound Control and Treatment: Animal Studies and Basic Foundation", Annals of Plastic Surgery, 38:6, pp. 553-562 (1997).*

(Continued)

*Primary Examiner*—Melanie J Hand
(74) *Attorney, Agent, or Firm*—Caesar, Rivise, Bernstein, Cohen & Pokotilow, Ltd.

(57) ABSTRACT

A medical device is provided that encloses a wound and promotes wound drainage by suction. The device includes an enclosure to be placed over a wound, adhesively connected to the skin around the wound by a flange. Gauze type packing cylinders can be placed in the wound, and suction is provided either by a bulb type pump, or by a pair of regulators. When regulators are used, one alternates the suction that it provides, and the other is continuous, such that the level of suction is periodically varied. The suction facilitates the transfer of liquid from the wound to the packing cylinders and from the packing out of the enclosure. A leak detector is optionally provided.

3 Claims, 9 Drawing Sheets

U.S. PATENT DOCUMENTS

| | | | |
|---|---|---|---|
| 2,113,253 A | 12/1935 | Gray | |
| 2,122,121 A | 2/1937 | Tillotson | |
| 2,195,771 A | 11/1937 | Estler | |
| 2,280,915 A | 4/1941 | Johnson | |
| 2,385,207 A | 6/1943 | Hunn | |
| 2,367,690 A | 7/1943 | Purdy | |
| 606,248 A | 5/1946 | Smith | |
| 2,524,750 A | 4/1947 | Bellinger | |
| 641,061 A | 8/1948 | McLaurin | |
| 2,524,195 A * | 10/1950 | Hoover | 604/13 |
| 2,727,678 A | 12/1955 | Henderson | |
| 3,026,874 A | 11/1959 | Stevens | |
| 3,042,041 A | 3/1960 | Jascalevich | |
| 3,042,037 A | 6/1961 | Scales | |
| 3,288,140 A | 11/1966 | McCarthy | |
| 3,367,332 A | 2/1968 | Groves | |
| 3,397,648 A | 8/1968 | Henderson | |
| 3,398,743 A | 8/1968 | Shalit | |
| 3,486,504 A | 12/1969 | Austin | |
| 3,556,096 A | 1/1971 | Fuller et al. | |
| 3,568,675 A | 3/1971 | Harvey | |
| 3,599,639 A | 8/1971 | Spotz | |
| 3,610,238 A | 10/1971 | Rich | |
| 3,616,156 A | 10/1971 | Scholl | |
| 3,874,387 A | 4/1975 | Barbieri | |
| 3,933,158 A | 1/1976 | Haverstock | |
| 3,954,105 A | 5/1976 | Nordby | |
| RE29,319 E | 7/1977 | Nordby | |
| 4,080,970 A | 3/1978 | Miller | |
| 4,112,947 A | 9/1978 | Nehring | |
| 4,180,074 A | 12/1979 | Murry | |
| 4,224,941 A | 9/1980 | Stivala | |
| 4,224,945 A | 9/1980 | Cohen | |
| 4,250,882 A | 2/1981 | Adair | |
| 4,261,363 A | 4/1981 | Russo | |
| 4,341,208 A | 7/1982 | Gordon | |
| 4,382,441 A | 5/1983 | Svedman | |
| 4,392,858 A | 7/1983 | George | |
| 4,399,816 A | 8/1983 | Spangler | |
| 4,444,548 A | 4/1984 | Anderson et al. | |
| 4,465,062 A | 8/1984 | Versaggi et al. | |
| 4,520,882 A | 6/1985 | van Nederveen | |
| 4,533,352 A | 8/1985 | Van Beek et al. | |
| 4,551,141 A * | 11/1985 | McNeil | 604/317 |
| 4,553,967 A | 11/1985 | Ferguson et al. | |
| 4,641,643 A | 2/1987 | Greer | |
| 4,710,165 A | 12/1987 | McNeil et al. | |
| 4,717,382 A | 1/1988 | Clemens | |
| 4,743,232 A | 5/1988 | Kruger | |
| 4,778,446 A | 10/1988 | Jensen | |
| 4,795,435 A | 1/1989 | Steer | |
| 4,820,284 A | 4/1989 | Hauri | |
| 4,925,447 A | 5/1990 | Rosenblatt | |
| 4,941,882 A | 7/1990 | Ward | |
| 4,969,880 A * | 11/1990 | Zamierowski | 604/305 |
| 4,969,881 A | 11/1990 | Viesturs | |
| 5,014,389 A | 5/1991 | Ogilvie | |
| 5,019,059 A | 5/1991 | Goldberg et al. | |
| 5,034,006 A | 7/1991 | Hosoda | |
| 5,086,763 A | 2/1992 | Hathman | |
| 5,088,483 A | 2/1992 | Heinecke | |
| 5,100,396 A | 3/1992 | Zamierowski | |
| 5,106,362 A | 4/1992 | Gilman | |
| 5,149,331 A | 9/1992 | Ferdman et al. | |
| 5,152,757 A | 10/1992 | Eriksson | |
| 5,160,315 A | 11/1992 | Heinecke | |
| 5,161,544 A | 11/1992 | Morris | |
| 5,167,613 A | 12/1992 | Karami | |
| 5,176,663 A | 1/1993 | Svedman | |
| 5,244,457 A | 9/1993 | Karami | |
| 5,261,893 A | 11/1993 | Zamierowski | |
| 5,358,494 A * | 10/1994 | Svedman | 604/313 |
| 5,437,651 A | 8/1995 | Todd | |
| 5,437,683 A | 8/1995 | Neumann | |
| 5,447,505 A * | 9/1995 | Valentine et al. | 604/304 |
| D364,679 S | 11/1995 | Heaton et al. | |
| 5,480,030 A | 1/1996 | Sweeney | |
| 5,484,399 A | 1/1996 | DiResta | |
| 5,527,293 A | 6/1996 | Zamierowski | |
| 5,549,584 A | 8/1996 | Gross | |
| 5,562,107 A | 10/1996 | Lavender et al. | |
| 5,636,643 A | 6/1997 | Argenta | |
| 5,645,081 A | 7/1997 | Argenta | |
| 5,701,917 A | 12/1997 | Khouri | |
| 5,840,049 A | 11/1998 | Turney | |
| 5,848,998 A | 12/1998 | Marasco, Jr. | |
| D406,899 S | 3/1999 | Cottle | |
| 5,931,797 A | 8/1999 | Turney et al. | |
| 5,951,533 A | 9/1999 | Freeman | |
| 6,071,267 A | 6/2000 | Zamierowaski | |
| 6,116,781 A | 9/2000 | Skeens | |
| 6,117,111 A | 9/2000 | Fleischmann | |
| 6,135,116 A | 10/2000 | Vogel | |
| 6,142,982 A | 11/2000 | Hunt | |
| 6,174,306 B1 | 1/2001 | Fleischmann | |
| 6,203,563 B1 | 3/2001 | Fernandez | |
| 6,242,665 B1 | 6/2001 | Malowaniec | |
| 6,283,931 B1 | 9/2001 | Augustine | |
| 6,323,386 B1 | 11/2001 | Stapf et al. | |
| 6,345,623 B1 | 2/2002 | Heaton et al. | |
| 6,458,109 B1 | 10/2002 | Henley et al. | |
| 6,557,704 B1 | 5/2003 | Randolph | |
| 2001/0020146 A1 | 9/2001 | Satterfield | |
| 2001/0029956 A1 | 10/2001 | Argenta | |
| 2001/0031943 A1 | 10/2001 | Urie | |
| 2001/0043943 A1 | 11/2001 | Coffey | |
| 2002/0016577 A1 | 2/2002 | Ohmstede | |
| 2002/0017304 A1 | 2/2002 | Heaton et al. | |
| 2002/0065494 A1 | 5/2002 | Lockwood et al. | |
| 2002/0068913 A1 | 6/2002 | Fleischmann | |
| 2002/0120185 A1 | 8/2002 | Johnson | |
| 2002/0143286 A1 | 10/2002 | Tumey | |
| 2002/0188279 A1 | 12/2002 | Waddell et al. | |
| 2003/0040687 A1 | 2/2003 | Boynton et al. | |
| 2003/0219469 A1 | 11/2003 | Johnson et al. | |

FOREIGN PATENT DOCUMENTS

| | | |
|---|---|---|
| EP | 0 853 950 A1 | 7/1998 |
| EP | 0 777 504 B1 | 10/1998 |
| GB | 1395799 | 3/1972 |
| GB | 1549756 | 3/1977 |
| GB | 2 099 308 A | 12/1982 |
| GB | 2 307 180 A | 11/1995 |
| GB | 2 329 127 A | 3/1999 |
| GB | 2 333 965 A | 8/1999 |
| GB | 2 336 546 A | 10/1999 |
| GB | 2 351 025 A | 12/2000 |
| GB | 2351 025 A | 12/2000 |
| GB | 2365 350 A | 2/2002 |
| GB | 2 356 148 A | 5/2003 |
| WO | WO 80/01139 | 6/1980 |
| WO | WO 89/05133 | 6/1989 |
| WO | WO 91/00718 | 1/1991 |
| WO | WO 96/05873 | 2/1996 |
| WO | WO 98/17329 | 4/1998 |
| WO | WO 00/21586 | 4/2000 |
| WO | WO 00/59418 | 10/2000 |
| WO | WO 00/59424 | 10/2000 |
| WO | WO 01/34223 A1 | 5/2001 |
| WO | WO 01/37922 A1 | 5/2001 |

WO    WO 01/85248 A1    11/2001

OTHER PUBLICATIONS

Dewan, An Alternative Approach to Skin Graft Donor Site Dressing, Jun. 1986. 2 Pages.

Alexander, Bacteriologic Comparison of Closed Suction and Penrose Drainage, Nov. 1984. 1 Page.

Genecov, A Controlled Subatmospheric Pressure Dressing Increases the Rate of Skin Graft Donor Site Reepithelialization, Mar. 1998. 7 Pages.

Biblehimer, Dealing With A Wound That Drains 1.5 Liters A Day, Aug. 1986. 3 Pages.

Morykwas, Effects of Varying Levels Subamospheric Pressure on the Rate of Granulation Tissue Formation in Experimental Wounds in Swine, Nov. 2003. 5 Pages.

Alexander, Emerging Concepts in the Control of Surgical Infections, Jun. 1974. 13 Pages.

Hathman Medical Products, 1 page.

Pescovitz. A History of Surgical Suction From Dieulafoy to Gomoco, Sep. 1989. 9 Pages.

Fowler, HowTo Cope When Your Patient Has An Entercutaneous Fistula, Mar. 1990. 4 Pages.

Landes, An Improved Suction Device for Draining Wounds, May 1972. 1 Page.

Svedman, Irrigation Treatment of Leg Ulcers, Sep. 1983. 3 Pages.

Jeter,New and Established Methods; Managing Draining Wounds and Fistulae, 1990. 7 Pages.

Shaer, Inexpensive Vacuum-assisted Closure Employing a Conventional Disposable Closed-suction Drainage System, Jan. 2003. 2 Pages.

Arnljots, irrigation Treatment in Split-Thickness Skin Grafting of Intrackable Leg Ulcers, 1985. 3 Pages.

Nakayama, A New Method For The Dressing of Free Skin Grafts, Dec. 1900. 4 Pages.

Rabinovici, New Sump Suction Appliance For Drainage of Enterocutaneous Fistulae, May 1988. 1 Page.

Abramson, A New, Soft, Triple Lumen, Overflow and Suction Drain, Sep. 1970. 3 Pages.

Ramirez, Opimal Wound Healing under Op-Site Dressing, Mar. 1973. 2 Pages.

Bellinger, An Original Drainage Cup Apparatus for Heostomies and Fistullas, Nov. 1949. 5 Pages.

Alexander, Prevnetion of Wound Infections—A Case for Closed Drainage to Remove Wound Fluids Defecient in OpsonicProtein, Jul. 1976. 5 Pages.

Gramm, Respitory Controlled Intermittent Inspiratory Pleural Drainage, Oct. 1984. 1 Page.

Schein, "Sandwich Technique" in the Management of the Open Abdomen, May 1986. 2 Pages.

Taira, Sternal Dehiscence "Delayed Primary Closure" for Complicated Cases, 1981. 3 Pages.

Hentzer, Suction Blister Transplantation For Leg Ulcers, 1975. 3 Pages.

Furnas, Suction Catheters for Open Technique of Skin Grafting in Fresh Wounds, Oct. 1976. 1 Page.

Jascalevich, Suction Cone: A New Apparatus for the Care of Heostomies, Fistulas and Draining Sinuses, Sep. 1960. 4 Pages.

Silvis, The Use Of Continuous Suction Negative Pressure Instead Of Pressure Dressing, Aug. 1955. 5 Pages.

Morykwas, Use of a Subatmospheric Pressure to Prevent Doxorubicin Extravasation Ulcers in a Swine Model, Jun. 1999. 4 Pages.

Morykwas, Morykwas, Use Of A Subatmospheric Pressure to Prevent Progression of Partial-Thickness Burns in a Swine Model, Jan. 1999. 7 Pages.

Vieira, Vacuum Assisted Closure in Calcanectomy for the Treatment of Chronic Calcaneal Osteomyelitis, Jun. 1997. 2 Pages.

Barker, Vacuum Pack Technique of Temporary Abdominal Closure: A 7 Year Experience with 112 Patients, Feb. 2000. 6 Pages.

Argenta, Vacuum-Assisted Closure: A New Method For Wound Control and Treatment: Clinical Experience , Jun. 1997. 15 Pages.

US 6,216,701, 04/2001, Heaton (withdrawn)

* cited by examiner

DEVICE FOR TREATING A WOUND

CROSS-REFERENCE TO RELATED APPLICATIONS

This application claims priority from U.S. provisional patent application No. 60/410,718, filed Sep. 16, 2002.

FIELD OF THE INVENTION

This invention relates to a medical device and related methods for treating wounds by promoting wound drainage.

BACKGROUND OF THE INVENTION

In the medical field there are many types of wounds that require treatment. In some instances they are post-operative wounds, but in other instances they can be open wounds that cannot yet be closed, as where infection sites exist, where open wounds require periodic application of medicine, or where the wounds are chronic non-healing pressure ulcers, venous ulcers, diabetic ulcers or where the wounds are too large to close surgically and must be allowed to heal on their own. In such cases, it is known that it can be desirable from the point of wound treatment, to apply a negative pressure or suction to the wound to remove fluids and exudates from the wound.

SUMMARY OF THE INVENTION

The present invention is directed to a medical device that encloses a wound and promotes wound drainage by suction.

The device of this invention includes a preferably anisotropic wound packing means, most preferably of the gauze type, that is configured and packed into the wound so as to encourage contraction of the wound in selected directions; such as contraction of the sides of the wound toward each other, toward eventual closure of the wound.

In one embodiment of the invention, suction is applied manually.

In another embodiment of the invention, suction is applied either via hospital wall suction, or via a portable pump.

Accordingly, it is a primary object of this invention to provide a medical device for treating a wound, in which an enclosure (sealing means) is placed over the wound and adhered to the skin disposed about a wound, with packing being placed into the wound for absorbing fluids from the wound to prevent or minimize pooling of liquid in the wound, and with suction being applied to the enclosure for facilitating transfer of fluids from the wound to the wound packing and to facilitate transfer of fluids from the wound packing out of said enclosure.

It is a further object of this invention to provide a medical device for treating a wound by promoting wound drainage, in which an enclosure (sealing means) is placed over the wound, and adhered to skin disposed about the wound, and wherein suction is applied to the enclosure for continuously applying suction to the wound, while periodically varying the level of suction applied to the wound.

It is another object of this invention to provide a medical device for treating a wound by promoting wound drainage, comprising an enclosure for placement over the wound and adhering it to skin around the wound, and to apply suction means to the enclosure for facilitating transfer of fluids from the wound to a wound packing that is placed in the wound, with the packing being configured to encourage contraction of the wound in preferred directions.

It is another object of this invention to accomplish the above object, wherein the packing is a gauze type material.

It is yet another object of this invention to accomplish each of the above objects, wherein the enclosure is provided with an openable and reclosable cover to facilitate access to the wound and ready re-sealing capability for the enclosure.

Other objects and advantages of the present invention will be readily understood upon a reading of the following brief descriptions of the drawing figures, detailed descriptions of the preferred embodiments, and the appended claims.

DETAILED DESCRIPTIONS OF THE PREFERRED EMBODIMENTS

Figure 1:
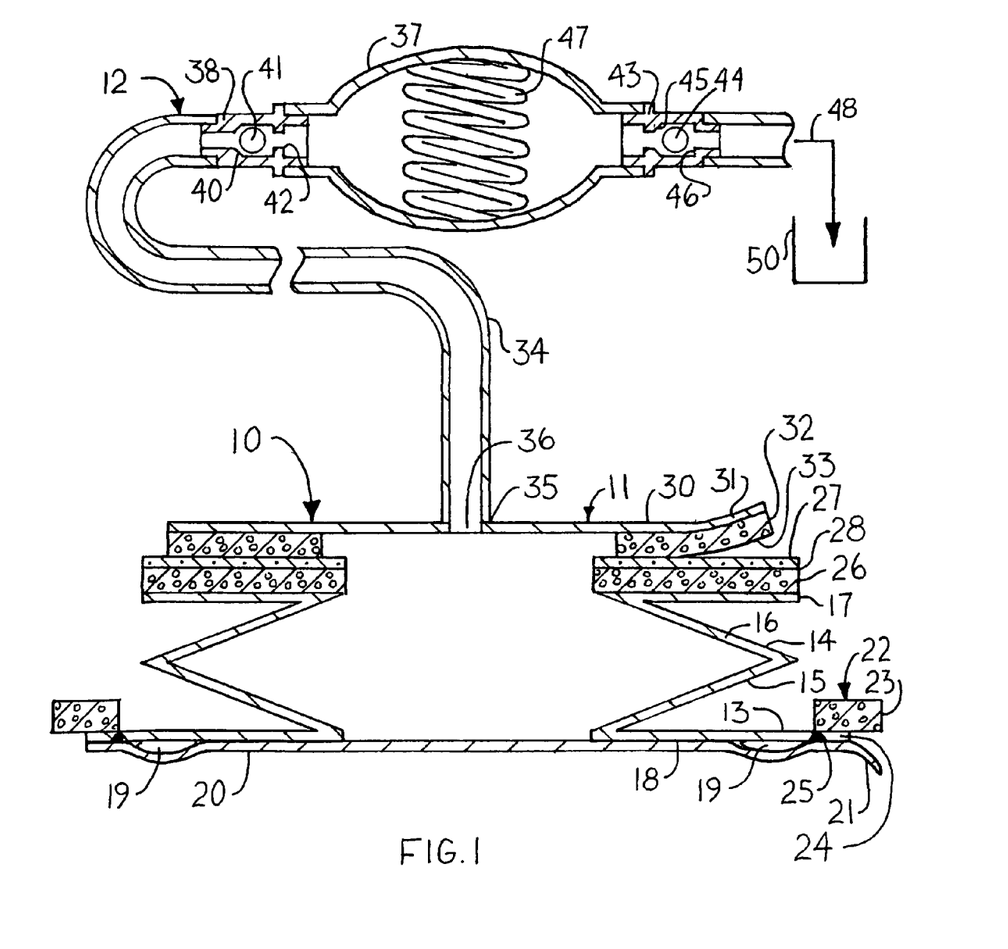
FIG. 1 is a cross-sectional view of a medical device for application to a wound, in which a bellows type film enclosure or sealing means is provided with an adhesive-covered lower surface having a release paper applied thereto at its lower end, and with a bulb type suction device connected to an openable enclosure on the device.

Referring now to the drawings in detail, reference is first made to FIG. 1, wherein the medical device 10 for treating a wound is shown, as comprising an enclosure component 11 and a suction component 12.

The enclosure component 11 includes a peripheral flange 13, a bellows 14 that includes a first bellows leg 15 and a second bellows leg 16. A top flange 17 is connected to the bellows leg 16, just as the bottom flange 13 is connected to the bellows leg 15, as shown. The flanges 13 and 17 and the bellows 14 are preferably comprised of a thin polyurethane film. An adhesive 18, that is preferably comprised of an acrylic skin contact adhesive, is disposed on the lower side of the flange 13, for adhesively engaging against skin (not shown in FIG. 1) peripheral to a wound. A release layer 20, of paper or film is carried against the adhesive layer 18 beneath the flange 13, with the release layer 20 sandwiching a gap-filling material 19 between the release layer 20 and the flange 13, but being readily removable by grasping an edge such as that 21 thereof, and pulling the same therefrom, to uncover the adhesive layer 18.

The flange 13 has, at its periphery, a frame 22 comprised of a semi-rigid polyethylene foam peripheral portion 23, preferably of the closed cell type, adhesively connected to a peripheral portion 24 of the flange 13 that is partially severed therefrom by a plurality of perforations 25, such that the frame 22, which provides support for the flange 13 and bellows 14 during the process of application about the wound of a patient, and may readily be removed therefrom, by severing the frame 23 from the rest of the flange 13 after such application, by tearing the same from the flange 13 along a peripheral severance line defined by the perforations 25.

The frame 22 supports the thin film of the flange 13, which would otherwise be difficult to handle once the release paper 20 is removed therefrom.

The upper flange 17 of the enclosure 11 is connected by means of a suitable adhesive, heat seal or the like to a layer 26 of polyethylene foam, which, in turn, is connected to a layer 27 of preferably polyethylene film by means of a suitable adhesive or heat seal, 28, as shown. A removable cover 30 for the enclosure 11 is comprised of a preferably vapor permeable polyurethane film 31, suitably secured to a preferably polyethylene foam peripheral layer 32 by means of a suitable adhesive, heat seal or the like. The layer 32 of foam carries a pressure sensitive acrylic adhesive layer 33 on its lower surface, for adhesive connection and disconnection, as desired, against the upper surface of the layer 27, whenever it is desired to remove the cover 30 from the remainder of the enclosure, for access to the wound, by simply grasping one edge of the cover 30, and lifting the same upwardly, as such lifting is shown to have begun at the right side of FIG. 1, for example. The adhesive 33 maintains its tackiness and can be repeatedly adhered to the surface 27 when the cover 11 is closed.

The bellows 14 acts as an extending means, allowing the flange 17 to float so that it can remain relatively wrinkle free. Maintaining the flange 17 relatively wrinkle free is important in that it allows the cover 30 to be releasably sealed to the layer 27. The ability of flange 17 to float also prevents direct application of force to the wound during reapplication of the cover, thus avoiding potentially painful occurrences to the patient.

It will be apparent that in the various illustrations of the various figures herein, the flange 13, the bellows 14, the flange 17, and the film 31 of the cover 30, are all extremely thin materials, but, as illustrated, are of exaggerated thickness so that the various layers may be readily seen and understood. Similarly, the various foam layers, such as those 26 and 32 are likewise of exaggerated thickness, for enabling visual presentation of the various layers, for facilitating an understanding thereof. Thus, the various layers of material illustrated in the drawings are not to scale. Rather, the enclosure is substantially flexibly conformable to the surface around the wound and is substantially non-protruding away from the skin surface around the wound when applied to the surface around the wound and when suction is applied.

Figure 2:
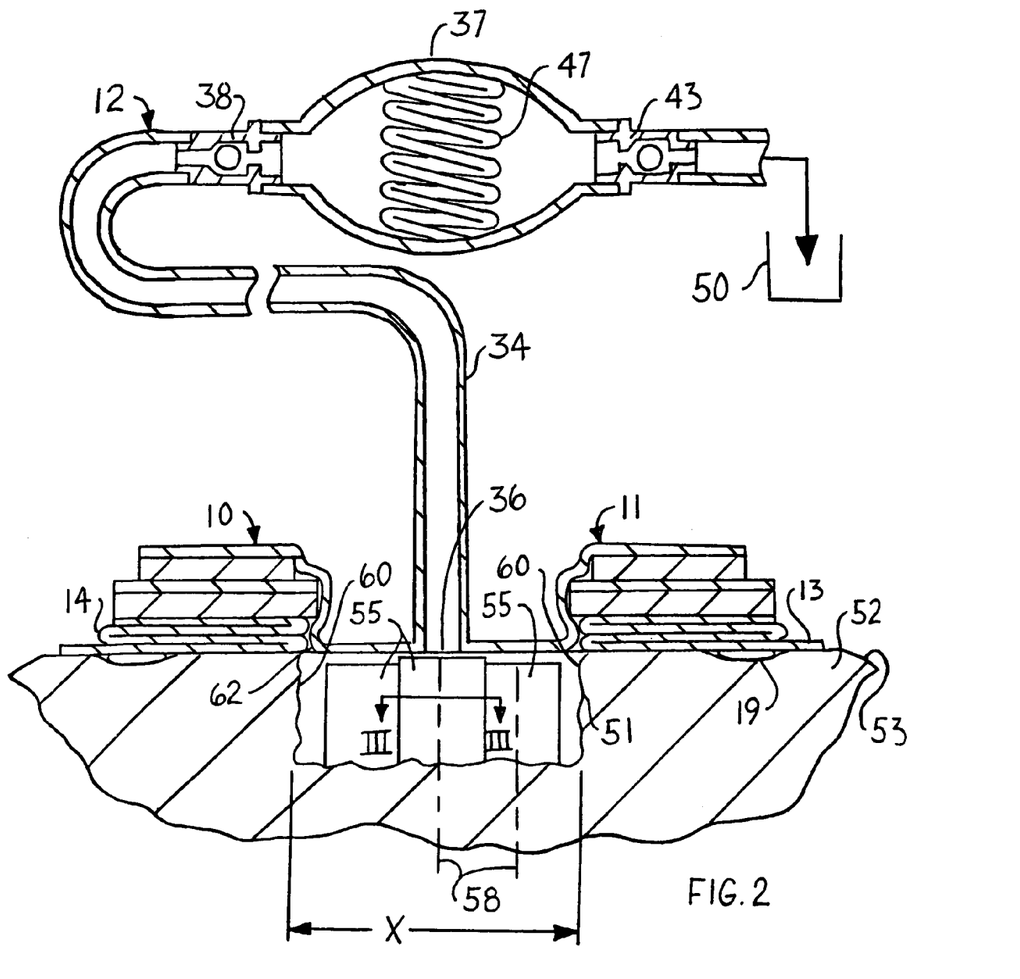
FIG. 2 is a sectional view similar to that of FIG. 1, but wherein the release paper has been removed from the bellows-type enclosure, and the enclosure is adhered to skin disposed about the wound, with rolls of packing being shown disposed in the wound, and with the bulb applying suction to the wound for gathering liquids therefrom for discharge to a container.

As can be seen in FIGS. 1 and 2, the enclosure 11, after removal of the release layer 20, leaves an opening that has a peripheral zone adapted to be applied to the skin surface around the wound, leaving an enclosure area inside the peripheral zone of a predetermined size, greater than the area of the wound to which the enclosure 11 is to be applied.

The cover 30 of the enclosure 11 has, on its upper surface, a suitable plastic tubing 34, heat sealed, or welded as shown at 35, to the upper surface of the layer 31, about an access opening 36 into the cover 30, as shown.

The tubing 34 thus connects the enclosure 11 to the suction device 12.

The tubing 34 is then connected to a flexible manually actuable bulb 37 through a caged ball type check valve 38 at the inlet thereof, with the ball 41 thereof adapted to seat against the seat 40 at the left side thereof, and with a suitable cage 42 limiting the rightward movement thereof into the bulb 37. The outlet 43 of the bulb comprises a check valve 43, likewise comprising a ball 44, adapted to seat against the seat 45, leftward thereof, and caged by a suitable cage 46 at the right side thereof, as shown in FIG. 1.

A spring element 47 is shown inside the flexible bulb 37, with the spring element 47 being significantly preloaded to provide a suction force when compressed, equivalent to approximately 100-125 mmHg. The wall of the bulb element 37 is sufficiently rigid to resist deformation under suction, but flexible enough to allow easy manual compression of the bulb and spring. The bulb element 37 may, for example, be fabricated from a material such as a flexible polyvinyl chloride or a silicone material.

Figure 1A:
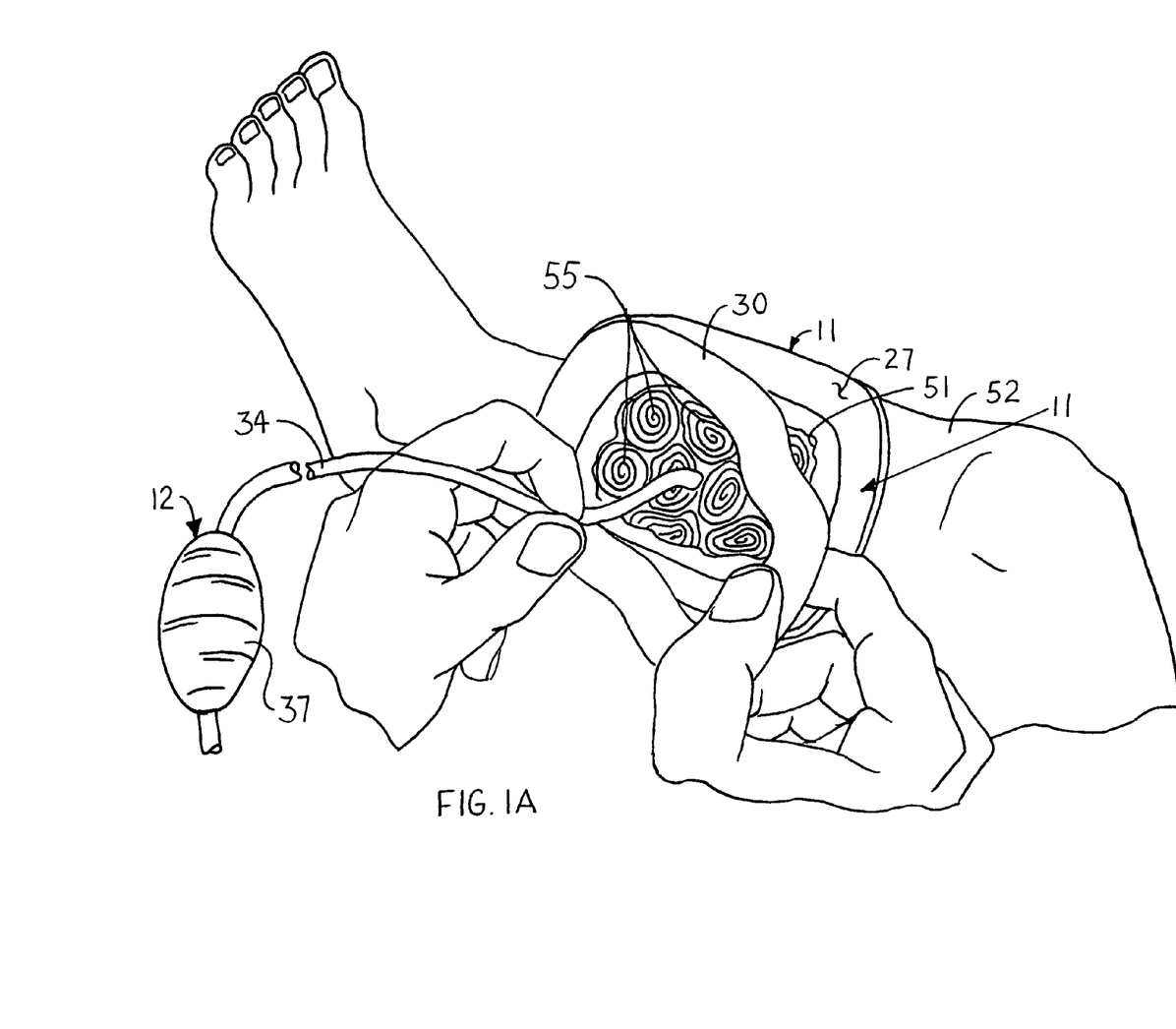
FIG. 1A is a perspective view of the device of FIG. 1, applied to a leg wound of a patient, showing the openable/reclosable feature of the enclosure of this invention.

With reference to FIG. 1a, it will be seen that the enclosure 11 is being applied to the leg portion of the body 52 of a patient, such that, after a flange 13 is adhesively secured to the skin 53 (not shown) of a patient, the cover 30 is openable and re-closable relative to the upper surface 27 such that packing cylinders 55 may be inserted into the wound 51, and then the cover 30 re-applied, so that suction can be drawn on the wound 51 via the suction device 12, by means of the squeezing of the bulb 37 drawing suction on the wound opening 51, via the tubing 34.

Thus, a pumping action can be obtained by squeezing the bulb 37 to expel contents, such as liquid removed from a wound, through check valve 43. The spring 47 and the natural resilience of the wall of the bulb 37 exert an outward force to draw fluids into the bulb 37, through the check valve at the inlet 38 to the bulb 37. The spring 47 provides a resistance to rapid decay of suction in the bulb 37. When the bulb 37 is exerting its suction force, the check valve 43 reacts against the suction and seals, such that the ball 44 seats against the seat 45, with the suction within the bulb 37 keeping the ball 41 unseated, so that fluid from a wound is drawn into the bulb 37 through the check valve 38. The tube 34 transmits the suction from the bulb 37 to the wound. When the bulb 37 is squeezed, and the ball 41 seats against the seat 40, such encourages the expulsion of fluids from the bulb 37 during the squeezing thereof.

Fluids discharged from the bulb, through the outlet check valve 43 thereof, are thus delivered via line 48 to a discharge container 50 or other available waste receptacle.

With reference now to FIG. 2, it will be seen that the device 10 of this invention is shown applied to a wound 51 in the body 52 of a patient, in that the flange 13 is adhesively sealed against the skin 53 of the body 52 of the patient, peripheral about the wound 51. Generally, first, prior to application of the enclosure 11 to the skin 53 of a patient, the release layer 20 is removed therefrom. Subsequently the flange 13 and gap filling material 19 of caulk-like paste for filling in any creases, gaps or the like, are simultaneously applied to the skin around the wound.

The paste or caulking that forms the gap-filling material 19, is preferably incorporated into the enclosure 11 during manufacture of the enclosure.

The gap-filling material is a flowable, conformable material that is substantially memory-free. That is, it can be pressed onto the skin, into imperfections, around hairs, and other imperfections and it will remain where it is applied, and will not return to its original shape or configuration. Thus, it will maintain its seal relative to skin imperfections, hairs, etc.

The gap-filling material will preferably be made in accordance with the teachings of U.S. Pat. No. 6,509,391 B2, the complete disclosure of which is herein incorporated by reference.

Also, either prior to applying the enclosure 11 to the skin 53 of a patient, or thereafter by removal of the removable cover 30, a wound packing material 55 is applied into the wound 51.

Figure 3:
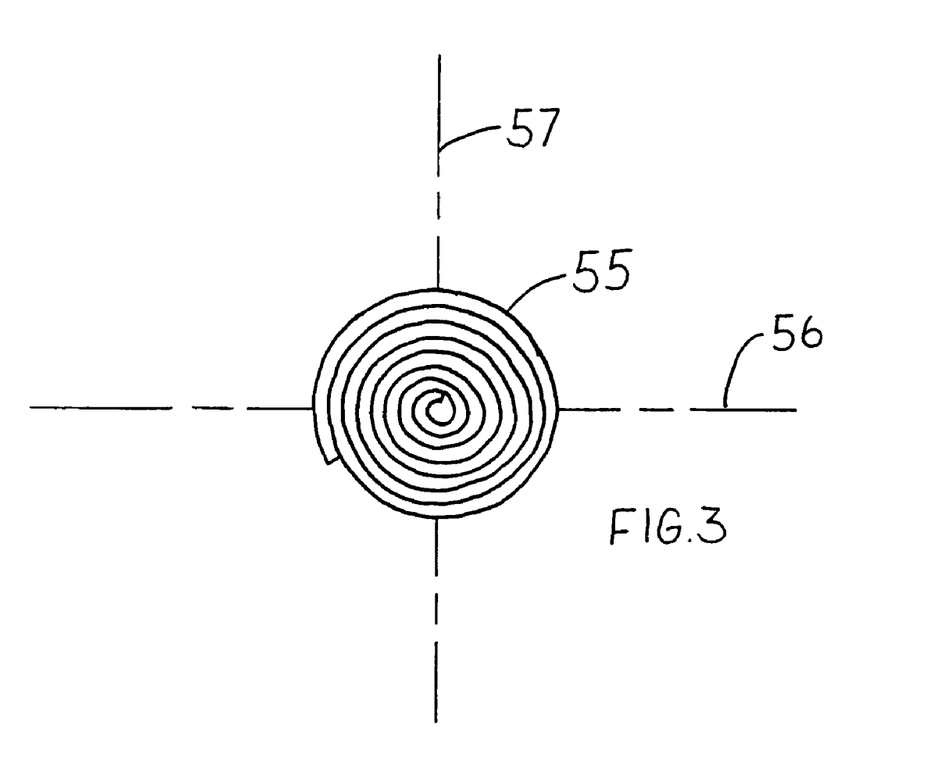
FIG. 3 is a cross-sectional view of a spirally wound roll of wound packing, taken generally along the line III-III of FIG. 2, to illustrate the packing in transverse section.

The wound packing material 55, as shown in FIG. 3 will preferably be comprised of an anisotropic wound packing, most preferably being a spirally wound, cylindrically configured winding of gauze, as shown in FIG. 3.

As shown in FIG. 2, the packing 55 may comprise a plurality of such cylindrical windings. The packing cylinders 55 provide a number of functions. The packing 55 prevents pooling of fluid in the wound cavity 51 and allows for wound drainage to be drawn from the wound surface and out of the enclosure 10. The packing cylinders 55 may be comprised of medical gauze. By using a construction for the packing 55 as shown in FIG. 3, such allows the gauze cylinders 55 to preferably collapse inwardly in the radial directions as indicated by the axes 56 and 57 as shown in FIG. 3, but not in the direction of the axes 58 as shown in FIG. 2. It will be seen that the axis 58 is in the vertical direction, facing upwardly or outwardly from the wound cavity 51, whereas the axes 56 and 57 face the sides 60 of the wound 51. This anisotropic behavior of the wound packing material can be utilized to impose a controlled directional strain on tissues in a medically preferred direction and amplitude necessary to optimize closure of difficult wounds.

Figure 4:
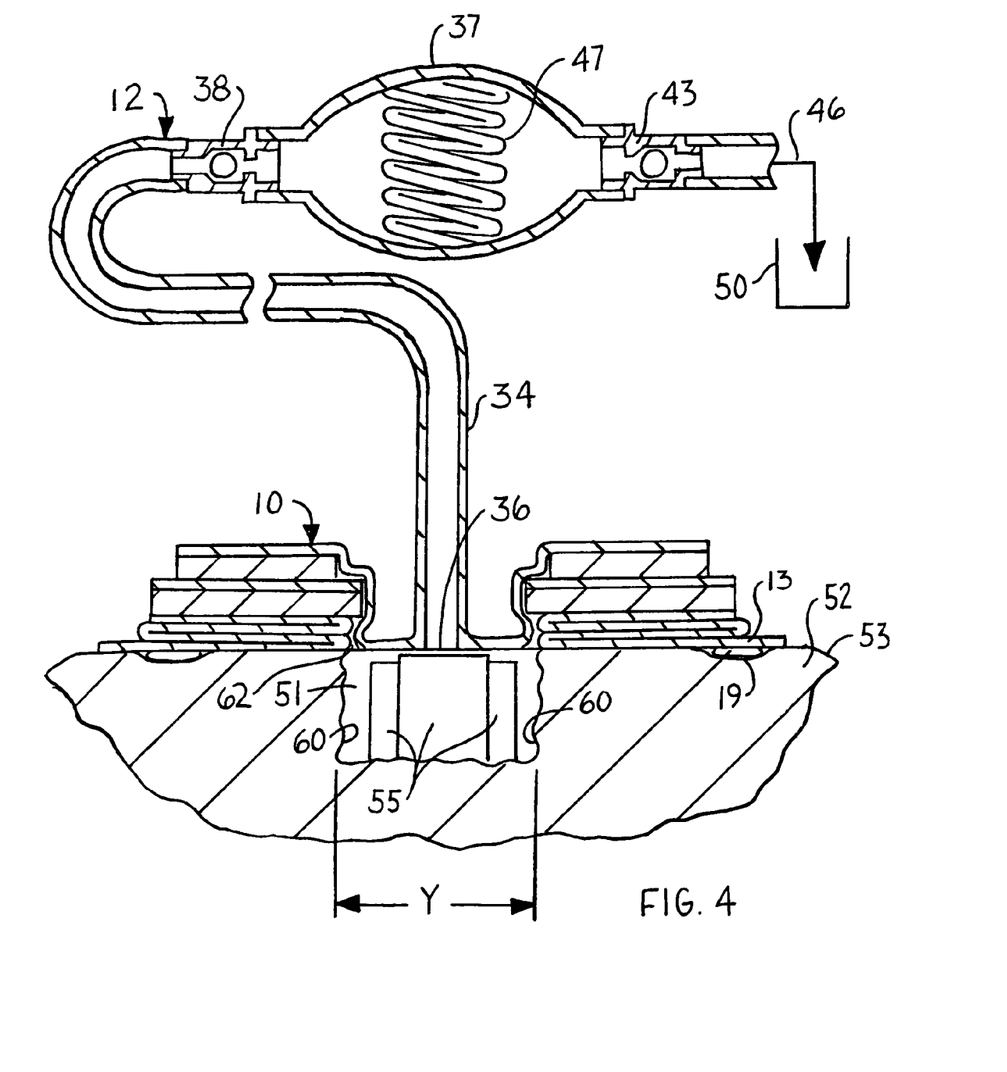
FIG. 4 is an illustration similar to that of FIG. 2, but wherein the wound is illustrated in a somewhat contracted manner to the illustration of FIG. 2.

Thus, as suction is applied to the wound 51, in the manner discussed above, into what would be the cavity 62 just above the wound, except that the cover 30 is sucked down to the packing 55 as shown in FIG. 2 and the wound 51 is encouraged to contract, side-to-side, and front-to-back, such that it tends to close peripherally, from a larger dimension "X" as shown in FIG. 2, to a smaller dimension "Y" as shown in FIG. 4, over time. The gauze cylinders, as illustrated, provide a versatile method for packing or filling the wound space that can be tailored to individual wound shapes.

Thus, it will be understood, that, in order to create a suction in zone 62 as shown in FIG. 2, the bellows 14 collapses to a position somewhat as shown in FIG. 2, from that shown in FIG. 1.

Figure 5:
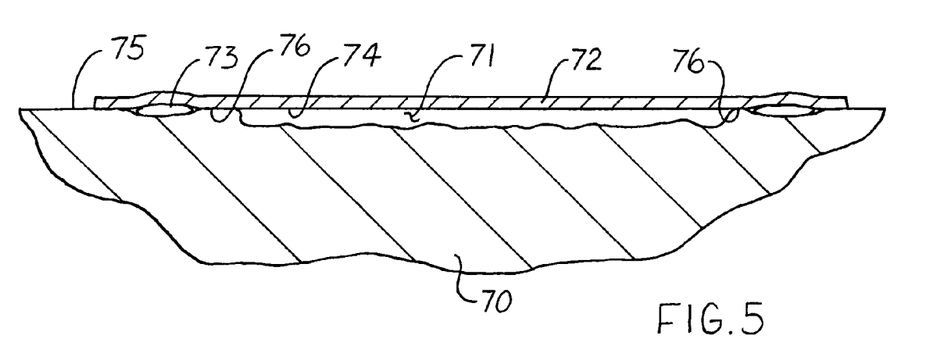
FIG. 5 is an illustration of another type of enclosure or sealing means for a wound embodying some of the features of the enclosures illustrated in FIGS. 1, 1A and 2.
Figure 5A:
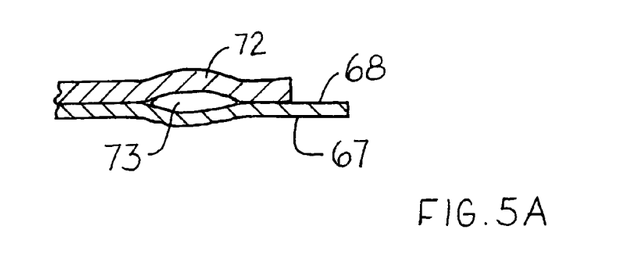
FIG. 5A is a fragmentary detail view of the right side of the enclosure of FIG. 5, prior to removal of a release strip from below the gap-filling material that is carried by the lower surface of the enclosure.

With reference now to FIG. 5, it will be seen that tissue or skin 70 is shown as having a wound 71 therein and an enclosure 72 of thin film is applied to the wound, with a gap-filling material 73 between the lower surface 74 of the enclosure 72 and the upper surface 75 of the skin, with said gap-filling material 73 functioning in the same manner as that 19 for the embodiment of FIG. 2, for example. The gap-filling material 73 is carried beneath the outer peripheral portion of the enclosure 72, therebeneath, and sandwiched between enclosure 72 and release liner 67. The liner 67 may be grasped by the tab 68 shown in FIG. 5A and removed from beneath enclosure 72 prior to enclosure 72 being applied to the surface 75 of the skin 70.

An adhesive 76 may be applied to the surface 74, for functioning together with the gap-filling material 73, to adhere the enclosure 72 to the surface 75 of the skin 70.

Figure 6:
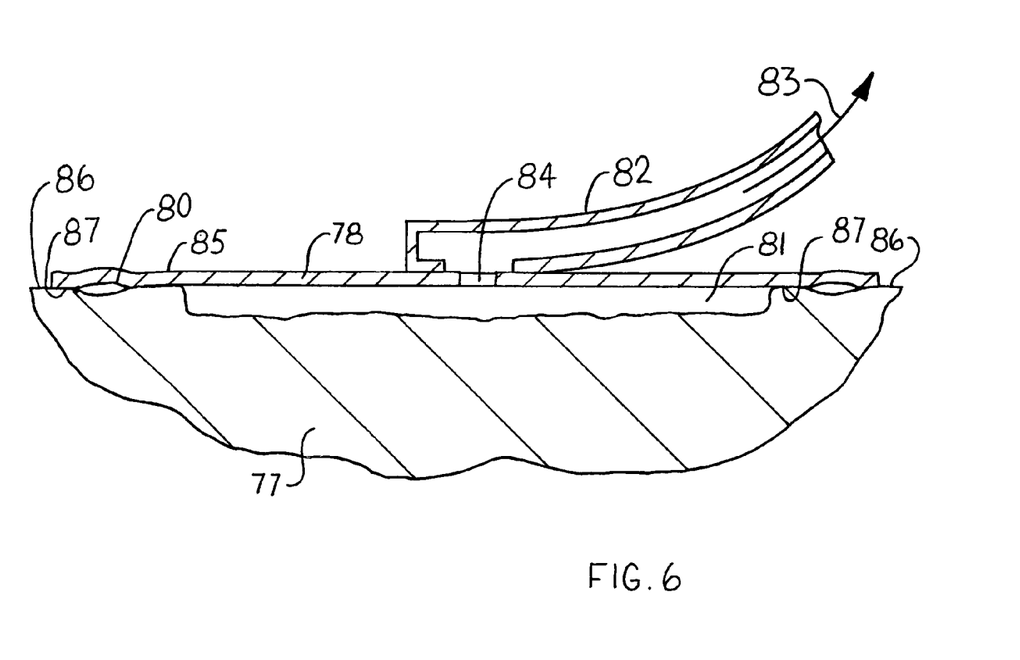
FIG. 6 is an illustration of another alternative enclosure or sealing means for a wound.

With reference now to FIG. 6, an illustration somewhat similar to that of FIG. 5 will be noted, in which the skin 77 has an enclosure 78 applied thereto, also of a thin film or the like, held thereon by a gap-filling material 80, similar to that discussed above with respect to the illustration of FIG. 5, and wherein the wound 81 is covered by the enclosure or sealing means 78, and wherein a partial vacuum or suction line 82 is provided, drawing a vacuum from the wound 81 in a direction of the arrow 83, via the access opening 84, for providing a reduced pressure in the wound 81, for healing purposes and to remove drainage materials. In addition thereto, the suction drawn via line 82 may also assist keeping the peripheral portion or flange 85 of the enclosure 78 adhered to the surface 86 of the skin, although an adhesive 87 may also be used against the undersurface of the flange 85, to further secure the flange 85 to the surface 86 of the skin, as may be desired, such adhesive functioning similarly to that described with respect to FIG. 2.

Figure 7:
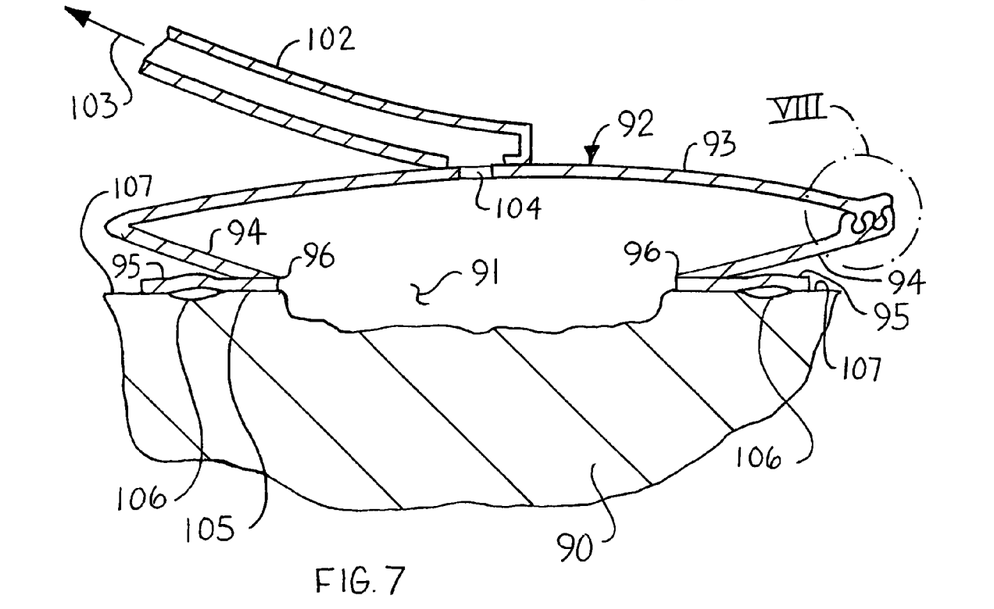
FIG. 7 is an illustration of yet another alternative enclosure or sealing means for a wound, in which a reclosable mechanical interlock is used.
Figure 8:
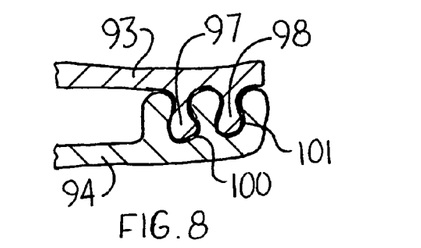
FIG. 8 is an enlarged detail view of a portion of FIG. 7, taken along detail VIII of FIG. 7, and wherein the reclosable mechanical interlock is more clearly illustrated.

With reference now to FIGS. 7 and 8, it will be seen that the skin 90 has a wound 91 therein and a thin film comprising an enclosure 92. The enclosure 92 includes an upper layer 93, a lower layer 94, and a flange 95. The flange 95 is hingedly connected to the lower layer 94 by a suitable heat seal or integral connection 96, extending around the periphery of the wound. The connection between the lower layer 94 and the upper layer 93 of the enclosure 92 may be a mechanical reclosable connection, whereby one, or a pair of male protrusions 97, 98, may engage in a corresponding one or more female recesses 100, 101, in a snap-fit engagement, to provide an air-tight seal completely or partially around the periphery of the connection of the lower layer 94 with the upper layer 93. In the embodiment shown in FIG. 7, the reclosable mechanical interlock as shown in FIG. 8 is not fully around the periphery of the connection of the layers 93 and 94 together, with such layers being hingedly together at the left end, with generally half or more of the connection being of the type of FIG. 8, around the periphery of the connection of the layers 93, 94 together. This will allow opening of the reclosable mechanical interlock shown in FIG. 8, for accessing the wound 91, for cleaning, replacement of gauze, etc.

In the embodiment of FIG. 7, a suction line 102 is used to draw suction in the direction of the arrow 103, from the wound 91, via the opening 104 in the film layer 93.

Additionally, in the embodiment of FIG. 7, an adhesive 105 may be used on the undersurface of the flange layer 95, in the manner described for the embodiments above. Furthermore, a gap-filling material 106 may also be used between the flange 95 and the outer surface 107 of the skin.

Occasionally, a wound might exist at a location where the enclosure is subjected to repeated motion, such as at a joint. For such a wound, it is desirable to use a combination of the mechanical interlock of FIG. 7 and the adhesive of FIG. 1.

Figure 9:
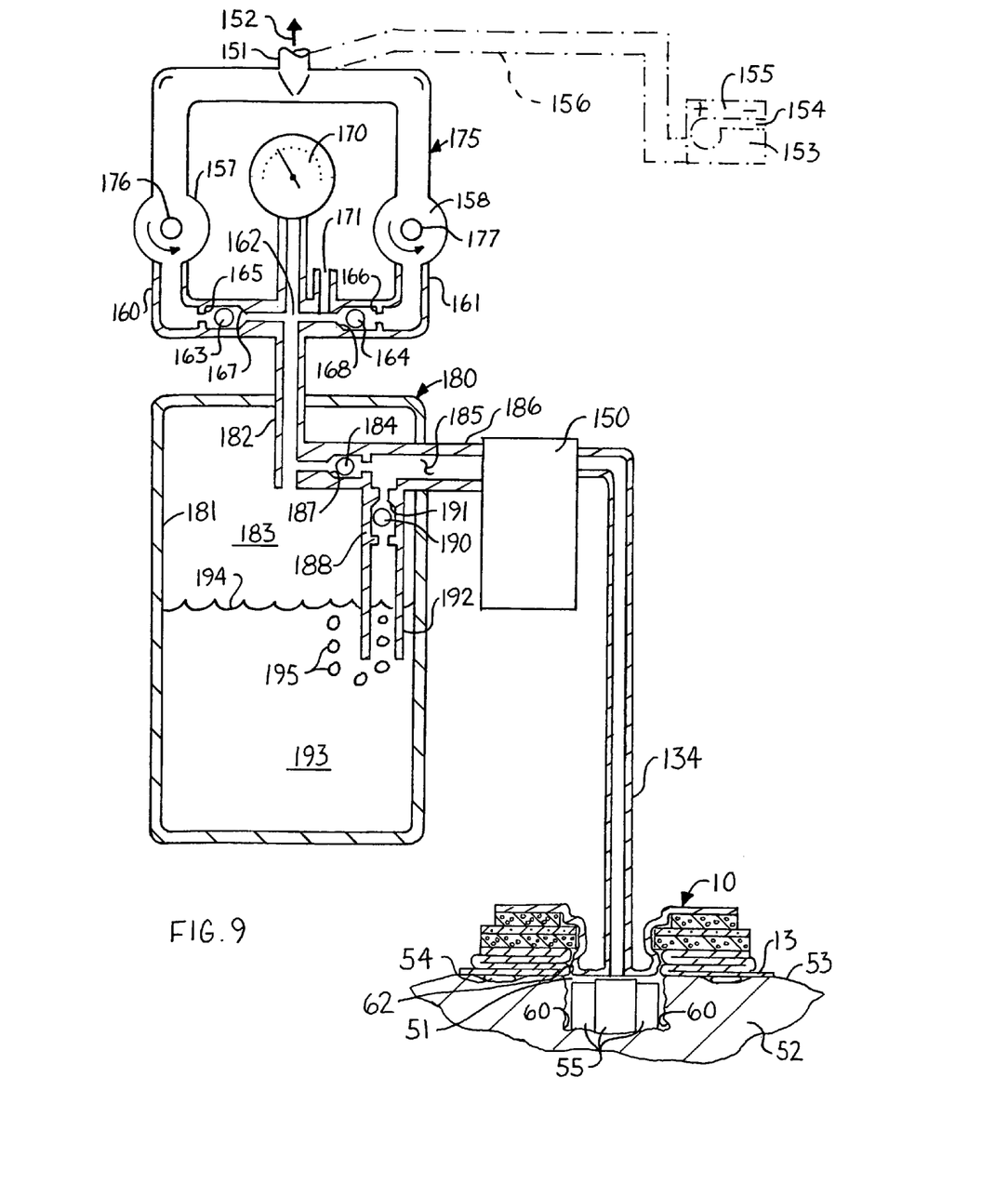
FIG. 9 is an illustration of the medical device of this invention, similar to that of FIG. 2, but wherein, instead of a bulb type suction device, there is shown a suction device in the form of a controller for hospital wall suction or a portable suction pump, for applying suction continuously at a fixed level and continuously at a level that is periodically varied. A leak indicating component is illustrated as well.

With reference to FIG. 9, an alternative source of suction is provided, wherein the enclosure 10 is constructed similar to that shown for FIGS. 1, 2 and 4, applied to the surface 53 of a patient 52 having a wound 51 therein, with packing 55.

However, in the embodiment of FIG. 9, the enclosure 10 is connected to a discharge container 150 via a preferably plastic conduit line 134.

In the embodiment of FIG. 9, a source of suction is applied at 151, in the direction of the arrow 152. The source of suction may ultimately be a hospital wall suction system, or the suction source may be a portable one, as shown at 153, in phantom, as an alternative. For a portable source of suction 153, a pump 154 or the like, or compressor may be driven via a battery 155, to create a suction that is delivered via suction line 156, to the suction line 151, in lieu of wall suction.

It will be apparent from the above that a portable source of suction as at 153 can employ various pumping devices, such as a 110 volt A.C. motor-vane pump, a diaphragm pump, a solenoid pump, or a D.C. motor pump, preferably of the rechargeable type. Alternatively, such means for providing suction can be microprocessor controlled.

Whatever the ultimate source of suction, the conduit 151 is connected to an intermittent regulator 157 and a continuous regulator 158, as shown. The outputs 160 and 161 of the respective regulators 157 and 158 are connected to a selector valve manifold 162 via suitable check valves that comprise balls 163, 164 having associated respective seats 167 and 168, suitable caged for limited ball movement by cages 165, 166.

A gauge 170 indicates the suction level being applied to the wound 51. When the intermittent regulator 157 cycles on, its check valve 163 permits high suction to the wound 51, which high suction overrides the setting of the continuous regulator 158. As the intermittent regulator 157 cycles off, the bleed orifice 171 allows the selector circuit to vent off to the setting established by the continuous regulator 158. Thus, the controller generally designated by the numeral 175 will alternately apply a low level of suction to the wound 51, or a high level of suction, with the suction in any event being continuous, but varying in level.

The level of suction provided at the low level via the continuous regulator 158 alone, may, for example, be at the level of 25 mmHg, and the high level of suction may, for example, as provided by the regulator 157, may be, for example, at the level of 125 mmHg.

The regulators 157 and 158 may be set for various levels of suction, as may be desired, by setting their control knobs 176, 177 respectively, to desired settings.

It will be understood that, instead of the ball check valves 38, 43, 163, 164, 184, 188, other valves may be used that would have the same function, such as duckbill valves or flapper valves, or the like.

A wall suction-based system is more ideally suited to patients that are bedridden in a hospital or skilled nursing facility, because wall suction lends itself to certain aspects of suction for wound healing. Wall suction can provide consistent suction that is independent of the volume of fluid collected. There is also a benefit that can be attributed to intermittently varying the level of suction that is applied between two distinct levels of suction. The benefit of alternating suction is that a periodic relaxation has been shown to improve blood flow and increase wound drainage. However, relief to atmospheric pressure can be problematic with respect to maintaining a seal around the wound. By intermittently varying the suction, such provides the benefit of intermitting, while maintaining some suction to maintain the effective seal of the enclosure about the wound. A similar system to that described above could be used to vary suction levels as well as switching between suction and positive pressure or per a defined algorithm.

There will preferably be disposed between the control system 175 and the closed discharge container 150, a leak detection device 180.

The leak detection device comprises a closed container 181, with a conduit 182 connecting it to the manifold 162 that comprises the high/low selector unit, for delivery of the suction from the interior of manifold 162 to the zone 62 of the wound 51, via the duct or tubing 134, and through the discharge container 150. The leak detecting unit 180 functions such that by drawing suction on the interior 183 of the unit 180, via line 182, the suction will be the same as the suction level 185 in line 186 connecting the interior 183 of the leak detection device 180 to the collection container 150, when the ball 184 is unseated relative to its seat 187. In the event that there is a leak between the leak detection unit 180 and the wound 51 or within the device 10, the resultant higher pressure in line 185 would cause the ball 184 to seat against the seat 187, such that the suction at zone 183 will draw air in line 185 past check valve 188 comprised of ball 190 and seat 191, such that air bubbles will pass outwardly of conduit 192, through liquid 193 as shown at 195, to bubble upwardly to liquid level 194 that is maintained in the unit 180.

The leak detection unit 180 helps to ensure that the system has minimal or no leaks and that suitable suction is maintained in the zone 62 of the wound dressing at the surface of the wound as well as within the cavities of the wound packing. Alternate systems that have been disclosed in the prior art involve microprocessors based systems that sound an alarm if the pump continues to run because adequate suction has not been generated. These systems result in high airflow prior to a leak being detected. High airflow has the detrimental effect of tissue drying along with elevated risk of infection, and is thus desirably avoided by this invention. The preferred approach described herein is based on flow as it is believed to be a superior method and provides the added ability to directly troubleshoot for actual leaks. Accordingly, the system 180 as described is a bubble detector. Preferably, the container 150 is of transparent construction to allow for ready viewing of the presence of any bubbles 195.

In the event of an air leak, such is evidenced as a stream of bubbles 195 in the liquid 194, such as water, that is in the container 151. Thus, there is provided a direct indication of any leaking. Leak resolution is apparent by the absence of bubbles.

The leak detector 180 should be tolerant to backflowing conditions that arise through the use of the intermittent application of suction as described above. Backflow of fluid is eliminated in the leak detector 180 by employing the check valves 184, 188, as described above. When the intermitting regulator 157 shifts to a lower suction level, there would be a tendency for air to rush into the collection unit 150 and the wound zone 62. Check valve 188 prevents loss of liquid 193 from the container 181 and valve 184 admits air into the circuit. The flow rate of air in the leak detector 180 can be determined by timing the bubble rate.

It will be apparent from the foregoing that various modifications may be made in the details of construction, as well as in the use and operation of the medical device of this invention, all within the spirit and scope of the invention as defined in the appended claims.

What is claimed is:

1. A medical device for treating a wound of a patient, the wound comprising a wound cavity having sides, an interior and at least one wound axis extending generally parallel to the skin of the patient contiguous with the wound cavity, said device being arranged for encouraging the contraction of the wound along the at least one wound axis, comprising:
    (a) an enclosure for engaging the skin of the patient over and around the wound and having an opening for communication with the interior of the wound cavity;
    (b) a separate anisotropic wound packing formed of plural rolls of gauze, each of said rolls having a longitudinal axis and at least one radial axis and comprising plural spiral layers wound about said longitudinal axis, said plural rolls of said wound packing being arranged to be tailored to individual wound cavity shapes and placed in the interior of the wound cavity with said at least one radial axis of each roll facing a side of the wound cavity and extending parallel to the at least one wound axis;

(c) an enclosure coupled to said wound packing, said enclosure being arranged to be separately placed over said wound packing after said wound packing has been placed in the interior of the wound cavity to produce an enclosed interior space in the wound in which said wound packing is located; and (d) a source of suction coupled to said enclosure to directly apply continuous suction via said opening in said enclosure to said enclosed interior space to draw fluid from the wound out of the enclosure, while causing said rolls of said wound packing to preferably collapse inward along said at least one radial axis when continuous suction is applied to the wound to impose a controlled directional strain on wound tissue along said at least one radial axis at an amplitude for optimizing closure of the wound, said wound packing also serving to prevent pooling of fluid in the wound cavity.

2. The medical device of claim 1, wherein said enclosure is arranged to create a substantially air-tight seal with the skin of the patient.

3. A method of controlling the direction of contraction of a wound of a patient, the wound comprising a wound cavity having sides, an interior and at least one wound axis extending generally parallel to the skin of the patient contiguous with the wound cavity, said method comprising the steps of:

(a) providing a separate anisotropic wound packing formed of plural rolls of gauze, each of said rolls having a longitudinal axis and at least one radial axis and comprising plural spiral layers wound about said longitudinal axis, said plural rolls of said wound packing being arranged to be tailored to individual wound cavity;

(b) placing said anisotropic wound packing in said wound cavity with said at least one radial axis of each roll facing a side of the wound and extending parallel to the at least one wound axis to allow a controlled strain to be imposed on the wound tissue;

(c) providing a separate enclosure engaging the skin of the patient over and around the wound, said enclosure having an opening in communication with the interior of the wound;

(d) sealing said wound with said anisotropic wound packing therein to produce an enclosed interior space in the wound in which said wound packing is located contiguous with said wound; and (e) providing a source of suction coupled to said enclosure to directly apply continuous suction via said opening in said enclosure to said enclosed interior space to draw fluid from the wound out of the enclosure, while causing said rolls of said wound packing to preferably collapse inward along said at least one radial axis when continuous suction is applied to the wound to impose a controlled directional strain on wound tissue along said at least one radial axis at an amplitude for optimizing closure of the wound, said wound packing also serving to prevent pooling of fluid in the wound cavity.

* * * * *